United States Patent [19]
Steininger et al.

[11] Patent Number: 5,425,767
[45] Date of Patent: Jun. 20, 1995

[54] ANCHOR FOR AN ARTIFICIAL LIGAMENT

[75] Inventors: Roland Steininger, Winterthur; Luigi Bivi, Basel, both of Switzerland

[73] Assignee: Sulzer Medizinaltechnik AG, Winterthur, Switzerland

[21] Appl. No.: 131,881

[22] Filed: Oct. 4, 1993

[30] Foreign Application Priority Data

Nov. 2, 1992 [EP] European Pat. Off. ............ 92810838

[51] Int. Cl.⁶ .............................................. A61F 2/08
[52] U.S. Cl. ......................................... 623/13; 606/60
[58] Field of Search ..................... 623/13, 11, 12, 16, 623/18; 606/60

[56] References Cited

U.S. PATENT DOCUMENTS 5,108,431  4/1992  Mansat et al. ...................... 623/13

FOREIGN PATENT DOCUMENTS 0465408  1/1982  European Pat. Off. .
0317406  5/1989  European Pat. Off. .
0330328  8/1989  European Pat. Off. .
0341198  11/1989  European Pat. Off. ............ 623/22
2586927  3/1987  France .
2676356  11/1992  France .

*Primary Examiner*—David Isabella
*Attorney, Agent, or Firm*—Townsend and Townsend Khoruie and Crew

[57] ABSTRACT

An anchor for an artificial ligament (1) in a bone (2). The anchor comprises a Y-shaped socket (3) having first and second arms (5, 6) configured at an acute angle with respect to each other. The first arm is sized to receive the ligament and has cross-grooves (15) for gripping the ligament. A bullet shaped clamp element (4) is rotatably mounted to the second arm. The clamp element also has grooves that directly contact the ligament to apply an oblique force against the ligament. The clamp element and the cross-grooves in the first arm completely surround and compress the ligament to frictionally secure the ligament to the socket. This configuration distributes the overall pressure so that the specific pressure at any one point is reduced.

11 Claims, 2 Drawing Sheets

ANCHOR FOR AN ARTIFICIAL LIGAMENT

BACKGROUND OF THE INVENTION

The invention deals with an anchor for an artificial ligament which is passed through a bone, the anchor consisting of a socket supported in the bone and a clamp element, where a ligament may be drawn into one arm of the socket. The clamp element is adjustable transversely to the ligament in order to apply a clamping force to the drawn-in ligament.

In the EP-A 0 465 408 a simple ligament anchor with a conical clamping socket is shown which is supported in a self-locking manner in a conical anchor socket. Similarly FR-A 2 586 927 and EP-A 0 232 049 show conical clamp elements which are pushed into an extension from the ligament like a sock in order to clamp it against an anchor socket. This anchor socket may in turn be reclamped which demands additional elements for it presupposes some skill on the part of the operating surgeon in order to coordinate the opposite movements of ligament stretching and clamping in such a manner that the ligament is secured with the desired prestress.

Moreover the EP-A 0 330 328 shows an anchor for a crucial ligament, in which through an axial offset an oblique shoulder is generated in the bore for receiving the ligament and by the ligament being compressed directly by the rounded tip of a grubscrew fitted transversely to the axis or indirectly via a deformable intermediate shell, between the tip and the oblique shoulder. For permanent location of the ligament the friction which is generated through pressure between the tip and the oblique shoulder must be adequate. Incautious clamping leads to peak pressures which injure the material of the ligament.

SUMMARY OF THE INVENTION

The problem of the invention is to achieve with certainty by simple means an anchor of the implanted ligament at a foreseen prestress. The solution of this problem is reached by the socket being formed towards the outside as a Y-tube the arms of which lie at an acute angle between 40° and 20° to one another. The tubular inner faces of the first arm for the ligament and of the second arm for the clamp element penetrate one another over the whole length of the bifurcation and the clamp element and the first arm exhibit grooves transverse to the ligament, which over a length amounting to more than one diameter of the ligament, together surround the ligament through 360° and compress it.

The solution has the advantage that the clamping force may be set from outside independently of the prestress of the ligament, and because of the large and structured clamping area any local destruction through peak pressures is prevented. The structuring of the clamping area along a fairly long length of the filament prevents it from flowing away. Through the employment of a socket which is made as a Y-tube a simple premachining in the bone results by the opening for passing through the ligament being widened to the diameter of a first arm and a second bore being made at the angle of the second arm standing out from it. With the socket inserted in the bone, the ligament may be drawn into it through the first arm and held under prestress by a spring balance, for example, while the clamping is effected independently through a clamp element in the second arm. The ligament may be drawn in off an endless stack to the appropriate length. After clamping and cutting off the ligament, the anchor terminates flush with the surface of the bone.

For the anchoring of crucial ligaments on the tibia side it is advantageous if—measured in the plane of the angle between the arms—the endface of the socket exhibits an angle of inclination of less than 80° to the first arm. Moreover for more stable anchoring one of the pair of arms may be continued in its direction beyond the point of intersection of the axes of the two arms. In order to give the socket a better hold in the direction of the tension, at least the continued arm via which the tension of the ligament is effected, has in the plane of the endface a projecting flap. The tip of the clamp element is made bullet-shaped and grooved in order to cooperate with the acute angle between the arms to generate a pressure area which extends over a greater length of the ligament. Moreover the clamp element may be made primarily as a clamp screw adjustable continuously by turning in the second arm or be made behind its tip as a socket with multiple longitudinal slits, the segments of which may be anchored via sawtooth grooves in opposing grooving in the second arm. In order to relieve the segments of permanent bending loading, after the ligament has been secured a pin may be inserted in the region of the core of the socket having the multiple longitudinal slits.

BRIEF DESCRIPTION OF THE DRAWING

The invention is described below with the aid of embodiments. There is shown in.

DESCRIPTION OF THE PREFERRED EMBODIMENT

In the Figures, anchors are shown for an artificial ligament such, e.g., as an artificial crucial ligament which is passed through a bone. The anchor consists of a socket which is supported in the bone and is made towards the outside as a Y-tube the arms of which lie at an acute angle to one another. The artificial ligament may be drawn into a first arm whilst in the second arm a clamp element is adjustable in the direction of the axis of the arm in order by its grooved shell to locate the ligament against the grooved inner face of the first arm.

Figure 1:
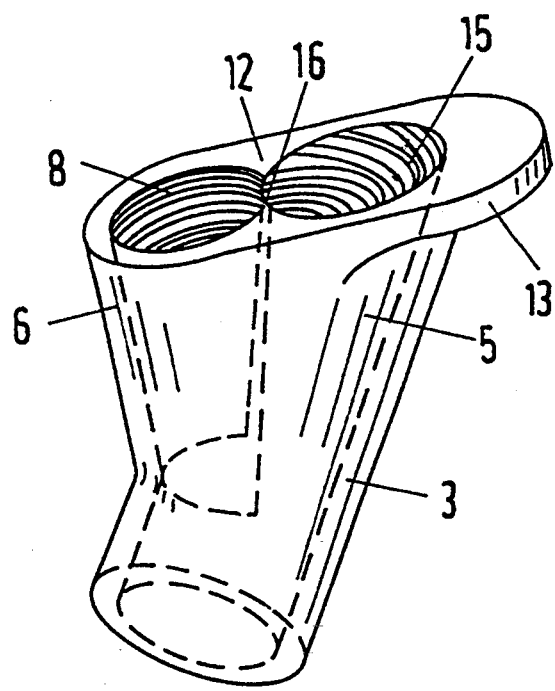
FIG. 1—the elevation of a socket without any clamp element.

In FIG. 1, a socket 3 in the form of a Y-tube is shown, the arms 5, 6 of which are shortened so much that no crotch is left and that the inner faces of the tubes of the arms 5, 6 penetrate one another or respectively continue into one another in an opening. A first arm 5 is continued further in the direction of its axis. Its inner face in the region opposite the second arm 6 standing away at the acute angle 7, is provided with crossgrooves 15. On the outside of it a flap 13 is fitted, projecting in the plane 12 of the endface of the socket 3. The second arm has on the inside of its tube a thread 8 which is provided as the support for a clamp element 4 in the form of a clamp screw 10.

Figure 2:
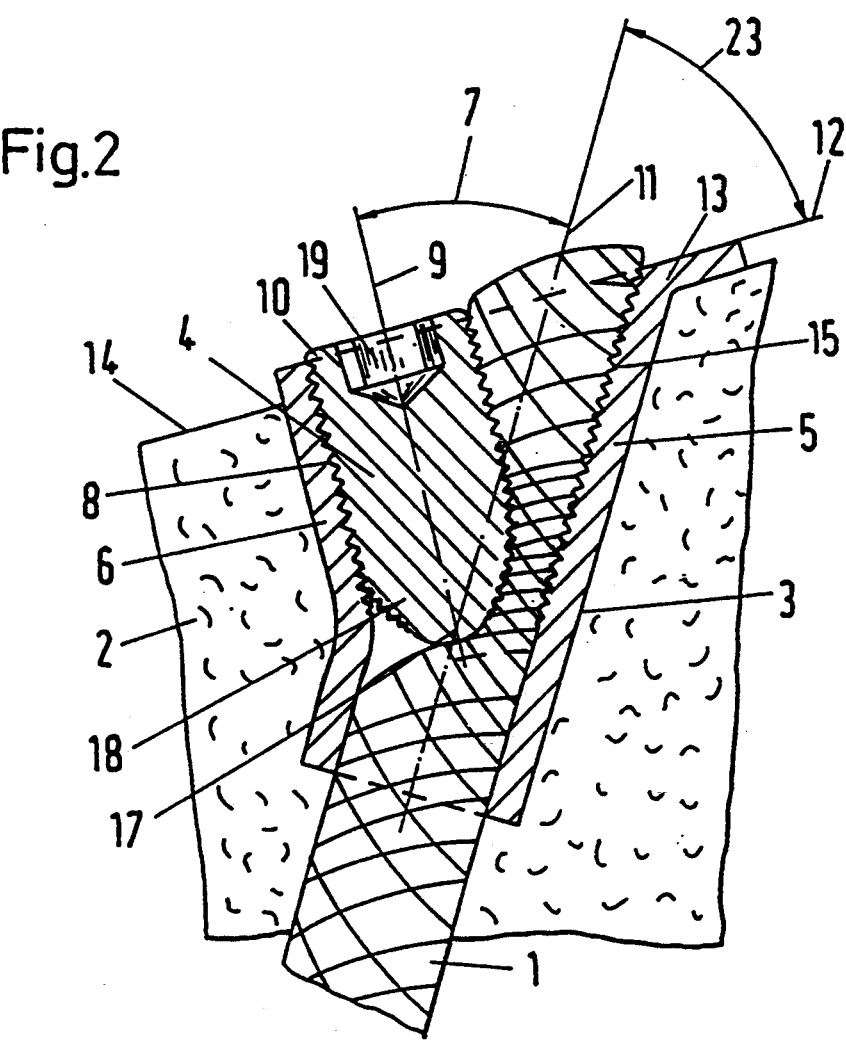
FIG. 2—diagrammatically the section through a ligament anchor inserted in the bone, which exhibits as the clamp element a clamp screw.
Figure 3:
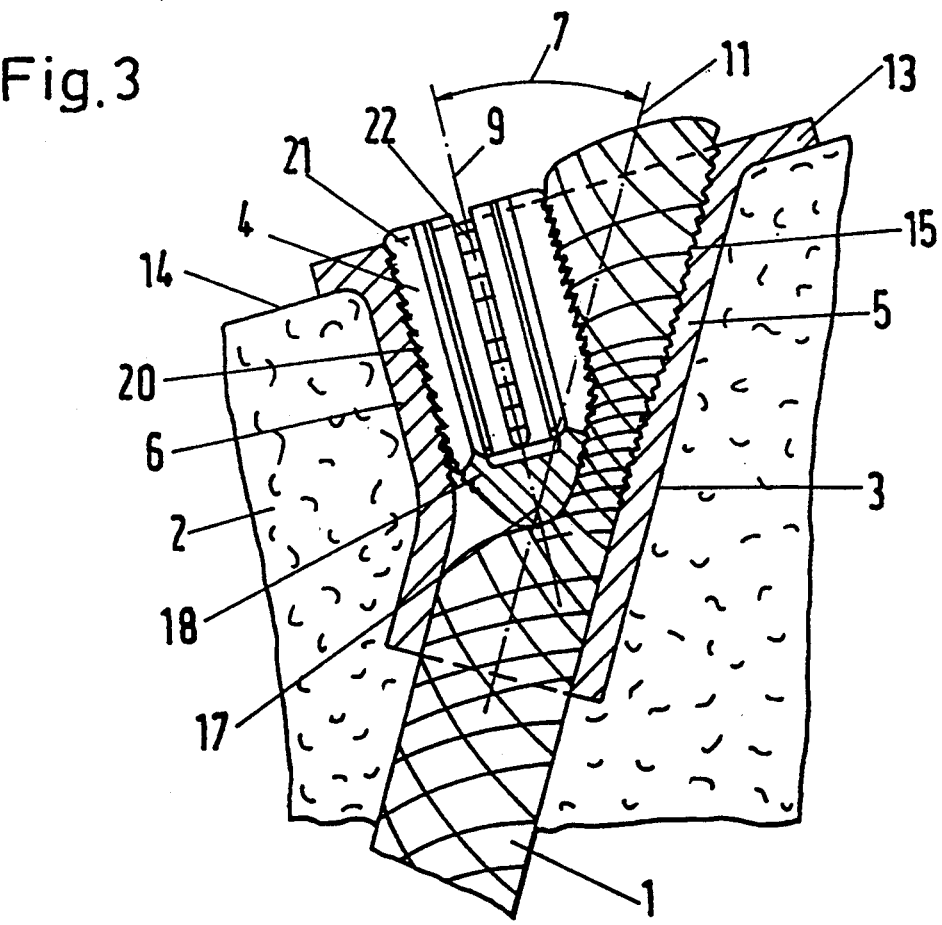
FIG. 3—diagrammatically the section through a ligament anchor inserted in the bone, which exhibits a clamp body with a slit socket and with toothed bending springs.
Figure 4:
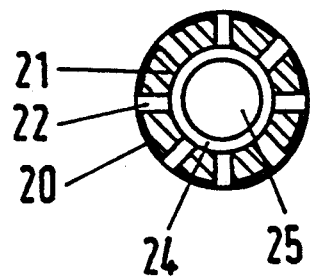
FIG. 4—diagrammatically the cross-section through a slit socket with toothed bending springs as in FIG. 3.

FIG. 2 shows the same socket 3 fitted in the bone 2 with an artificial ligament 1 drawn in through the bone. The two arms 5, 6 lie at an angle 7 between 40° and 20° to one another and have an opening 16 through between them by their intersecting one another. Measured in the plane of the two axes 11 and 9 of the arms the plane 12 of the endface of the socket 3 lies at an angle of inclination 23 of less than 80° to the axis 11 of the shank of the first arm 5 which is continued in its direction beyond the point 17 of intersection of the two axes 11, 9 of the arms. A thread 8 is cut in the second arm 6 and interrupted by the opening 16 and against it a clamp element 4 of bullet shape 18 bears by an external thread, being movable as a clamp screw 10 by an internal hexagon 19. The clamping of the ligament 1 when it has been drawn in is effected by one sideface of the elongated bullet shape of the clamp screw 10, which presses the ligament 1 sideways against the wall of the first arm 5 and generates an elongated pressure zone. For assisting the hold of the ligament 1 the crossgrooves 15 are carried on into the pressure zone and may exhibit sharp edges. The hold is increased to 360° by the threaded part of the clamp screw 10 resting against the ligament 1 in the opening 16. The crossgrooves 15 may also exhibit a slight inclination if they are generated as an internal thread by a screw tap. Stepless setting of the clamping force against a prestressed ligament 1 is also possible by the clamp screw 10. A further bearing of the clamp element 4 is shown in FIGS. 3 and 4. The rear part of the bullet-shaped body has the form of a socket with multiple longitudinal slits and a cylindrical cavity 24. Longitudinal slits 22 divide the shell into bending springs 21. These exhibit on their outside in the longitudinal direction a set of sawteeth 20 which under the prestress from the bending springs 21 rest against an opposing set of teeth on the inner face of the second arm 6. The set of teeth is so designed that in a self-locking manner it acts against the clamp element 4 sliding backwards. For clamping the ligament the clamp body 4 must be driven forwards from catch-station to catch-station until the necessary clamping force is reached. This is done, for example, by a plunger (not shown here) which rests against the bottom 25 of the cylindrical cavity 24 and exhibits a smaller diameter than the latter so that upon running the clamp element 4 in towards the longitudinal axis the bending springs 21 can deform. If the bending springs 21 are of relatively weak design, after reaching the clamping position a locking pin or locking screw may be fastened in the cylindrical cavity 24 in order to prevent springing back or fatigue of the bending springs 21.

With the anchor inserted, the tension in the artificial ligament 1 acts in the direction of the axis 11 of the first arm 5. The areas outside the inner diameter of the first arm 5 and projected onto a plane lying perpendicular to the axis 11 of the arm are to be regarded as effective areas for the transmission of force to the bone 2. These areas are the flap 13 and the projected area of the second arm 6. In the event that this area should be considered too small the flap 13 may as indicated in FIG. 3 be carried round onto the opposite side in the plane 12.

A number of sockets 3 are available to the operating surgeon for the anchor, which differ by different angles of inclination 23 of the plane 12 of their endface to the axis 11 of the shank. Hence the anchor can be adapted to the direction of pull of the artificial ligament 1.

We claim:

1. An anchor for an artificial ligament to be attached to a bone, the anchor comprising:

a socket for positioning in the bone, the socket having first and second intersecting openings, each opening defining a longitudinal axis that form an acute angle with respect to each other, the first arm being sized to receive the ligament;

a clamp element adjustably mounted to the second arm, the clamp element being adapted for directly contacting the ligament to apply an oblique force against the ligament;

the clamp element and the first arm having grooves, the grooves surrounding and compressing a portion of the ligament when received by the first arm to frictionally secure the ligament to the socket.

2. The anchor of claim 1 wherein the clamp element directly contacts the ligament along a length that is greater than a diameter of the ligament.

3. The anchor as in claim 1 wherein the socket has an endface, the endface having an angle of inclination to the first arm of less than 80 degrees.

4. The anchor as in claim 1 wherein the first and second arms each have an axis, the axes intersecting at a point, the first arm extending beyond the point of intersection of the two axes.

5. The anchor as in claim 3 wherein the first arm has a flap bearing against the bone, the flap being exterior to the socket and parallel with the endface.

6. The anchor as in claim 1 wherein the clamp element is a clamp screw rotatably adjustable within the second arm, the screw having a bulletshaped grooved tip.

7. The anchor as in claim 6 wherein the clamp element comprises an outer shell surrounding a cylindrical cavity, the shell being divided by longitudinal slits into bending springs, each bending spring having longitudinal teeth, the second arm having teeth that mate with the longitudinal teeth to form a one-way lock, the one-way lock allowing the clamp element to enter the second arm and preventing the clamp element from exiting the second arm.

8. An anchor as in claim 7 further including a locking-pin mounted within the cylindrical cavity to secure the clamping element within the second arm.

9. An anchor for an artificial ligament to be attached to a bone, the anchor comprising:

a Y-shaped socket for placement in the bone, the socket having first and second arms intersecting openings, each opening defining a longitudinal axis that form an acute angle with respect to each other, the first opening being sized to receive the ligament;

a clamp element adjustably mounted within the second opening, the clamp element being adapted for directly contacting a portion of the ligament; and the first opening and the clamp element compressing the portion of the ligament when received by the first opening to provide sufficient pressure to secure the ligament to the socket, the portion being longer than a diameter of the ligament so that the pressure is distributed along the portion of the ligament contacted by the clamp element.

10. An anchor for an artificial ligament to be attached to a bone, the anchor comprising:

a generally Y-shaped socket for placement in the bone, the socket defining first and second intersecting openings which are angularly inclined with respect to each other at an oblique angle, the first opening being sized to receive therein the ligament; and a clamp element having a face with grooves, the face being disposed in the second opening and movable towards the first opening for applying a holding force to the ligament disposed therein such that a section of the ligament substantially conforms to the grooves of the face, the clamping element having a face adapted to contact the ligament when it is disposed in the first opening and which applies the holding force over the section of the ligament which is longer than a diameter of the ligament to thereby retain the ligament to the socket, reduce pressure between the ligament and the face and prevent the holding force from damaging the ligament.

11. An anchor according to claim 10 wherein the face has a convex shape.

* * * * *